(12) United States Patent
Atwell (10) Patent No.: US 11,540,709 B2
(45) Date of Patent: Jan. 3, 2023

(54) SURGICAL DEVICE HAVING AN ELONGATE SHAFT WITH A RETRIEVAL LUMEN

(71) Applicant: GYRUS MEDICAL LIMITED, Cardiff (GB)

(72) Inventor: Tony Atwell, Newport (GB)

(73) Assignee: GYRUS MEDICAL LIMITED, Cardiff (GB)

( * ) Notice: Subject to any disclaimer, the term of this patent is extended or adjusted under 35 U.S.C. 154(b) by 914 days.

(21) Appl. No.: 16/250,281

(22) Filed: Jan. 17, 2019

(65) Prior Publication Data

US 2019/0223851 A1 Jul. 25, 2019

(30) Foreign Application Priority Data

Jan. 22, 2018 (GB) ..................... 1800979

(51) Int. Cl.
*A61B 1/313* (2006.01)
*A61B 1/00* (2006.01)
(Continued)

(52) U.S. Cl.
CPC ........ *A61B 1/3132* (2013.01); *A61B 1/00154* (2013.01); *A61B 1/307* (2013.01);
(Continued)

(58) Field of Classification Search
CPC .......... A61B 17/00234; A61B 1/00154; A61B 1/04; A61B 1/307; A61B 1/3132;
(Continued)

(56) References Cited

U.S. PATENT DOCUMENTS 5,190,555 A 3/1993 Wetter et al.
5,192,284 A 3/1993 Pleatman
(Continued)

FOREIGN PATENT DOCUMENTS

CN 107095712 A 8/2017
EP 2184014 A2 5/2010
(Continued)

OTHER PUBLICATIONS

Jun. 27, 2018 Search Report issued in European Patent Application No. GB1800979.5.

*Primary Examiner* — Anh Tuan T Nguyen
*Assistant Examiner* — Shankar Raj Ghimire
(74) *Attorney, Agent, or Firm* — Oliff PLC (57) ABSTRACT

A surgical device comprises an elongate shaft (12) which extends from a proximal end region to a distal end region thereof, the shaft (12) defining a first lumen (14) for receiving an elongate camera device therein, a second lumen (16) for receiving a tissue manipulation device therein, and a third lumen (18) for receiving a tissue retrieval device therein, the first, second and third lumens (14, 16, 18) extending from the proximal end region to the distal end region of the elongate shaft, and having respective open ends at the distal end region of the elongate shaft. The surgical device further comprises an elongate camera device which extends along the first lumen, a tissue manipulation device which extends along the second lumen, and a tissue retrieval device which extends along the third lumen.

8 Claims, 6 Drawing Sheets

(51) Int. Cl.
*A61B 17/00* (2006.01)
*A61B 1/307* (2006.01)
*A61M 25/00* (2006.01)
*A61B 17/22* (2006.01)

(52) U.S. Cl.
CPC ............... *A61B 17/00234* (2013.01); *A61B 2017/00287* (2013.01); *A61B 2017/00367* (2013.01); *A61B 2017/00477* (2013.01); *A61B 2017/22074* (2013.01); *A61B 2217/005* (2013.01); *A61M 25/0023* (2013.01)

(58) Field of Classification Search
CPC ........... A61B 2017/00287; A61B 2017/00367; A61B 2217/005; A61B 1/00135; A61B 17/221; A61B 2017/22072; A61B 2017/22079; A61M 25/0023
See application file for complete search history.

(56) References Cited

U.S. PATENT DOCUMENTS

| | | | |
|---|---|---|---|
| 5,759,187 A | 6/1998 | Nakao et al. | |
| 6,221,007 B1* | 4/2001 | Green | A61B 1/00052 600/104 |
| 2004/0225192 A1* | 11/2004 | Young | A61B 17/3423 600/204 |
| 2005/0119525 A1* | 6/2005 | Takemoto | A61B 1/00137 600/114 |
| 2005/0222581 A1* | 10/2005 | Fischer | A61B 1/00135 606/108 |
| 2011/0184434 A1* | 7/2011 | Parihar | A61B 17/00234 606/114 |
| 2011/0184435 A1* | 7/2011 | Parihar | A61B 17/00234 606/114 |
| 2011/0184436 A1* | 7/2011 | Shelton, IV | A61B 17/00234 606/114 |
| 2011/0190782 A1* | 8/2011 | Fleming | A61B 17/00234 606/114 |
| 2012/0083797 A1* | 4/2012 | Cabrera | A61B 17/00234 606/114 |
| 2012/0089151 A1* | 4/2012 | Taylor | A61B 17/221 606/114 |
| 2012/0179165 A1* | 7/2012 | Grover | A61B 17/00 606/114 |
| 2013/0116592 A1* | 5/2013 | Whitfield | A61B 10/02 600/562 |
| 2015/0209020 A1* | 7/2015 | Parihar | A61B 17/00234 493/395 |
| 2015/0250486 A1* | 9/2015 | Taylor | A61B 17/221 606/114 |
| 2015/0272620 A1* | 10/2015 | Zisow | A61B 17/3205 600/204 |
| 2015/0297204 A1* | 10/2015 | Horton, Jr. | A61B 17/00234 606/114 |
| 2016/0157843 A1* | 6/2016 | Dickson | A61B 17/221 606/47 |
| 2017/0020500 A1 | 1/2017 | Taylor et al. | |
| 2017/0128088 A1* | 5/2017 | Kahle | A61B 17/221 |
| 2017/0311964 A1* | 11/2017 | Desai | A61B 17/00234 |
| 2018/0042462 A1* | 2/2018 | Yanuma | A61B 18/1492 |
| 2018/0303511 A1* | 10/2018 | Graf | A61B 17/32056 |

FOREIGN PATENT DOCUMENTS

| | | |
|---|---|---|
| GB | 2551024 A | 12/2017 |
| WO | 2016028789 A2 | 2/2016 |
| WO | 2016079752 A1 | 5/2016 |
| WO | 2016168865 A1 | 10/2016 |
| WO | 2017/192452 A1 | 11/2017 |

* cited by examiner

SURGICAL DEVICE HAVING AN ELONGATE SHAFT WITH A RETRIEVAL LUMEN

The present invention relates to surgical devices, and, in particular, to surgical devices for endoscopic or laparoscopic surgical procedures.

BACKGROUND OF THE INVENTION

Endoscopic and laparoscopic surgical techniques are well-known, particularly for abdominal operations, and make use of a camera (an endoscope or a laparoscope) inserted into the body of a patient via a relatively small incision, or a natural orifice such as the urethra. Other tools and devices are inserted into the body of the patient also through relatively small incisions. The camera allows the surgeon to view the tissue needing surgery without the need for large incisions required by traditional surgery techniques. Endoscopic surgery, and laparoscopic surgery are sometimes referred to as "keyhole surgery" or "minimally invasive surgery" due to the small size of incisions required.

In procedures that involve removal of at least part of an organ, or a tumour associated with an organ, there is a need for a retrieval bag that can carry the removed tissue from the body cavity. For example, procedures on organs such as the bladder, gall bladder, appendix, colon, spleen, ovary, lymph nodes, lung, etc. may require tissue removal.

The retrieval bag systems currently on the market generally involve totally disposable instruments. For example, U.S. Pat. No. 5,192,284 discloses a surgical collector and extractor for specimen removal through a cannula in a laparoscopic procedure. The device includes a flexible bag for collection purposes. U.S. Pat. No. 5,190,555 discloses a tissue collection device having a flexible bag activated by a drawstring. Other types of tissue retrieval bags are disclosed in, for example, WO2016079752 which is an isolation bag, and WO2016028789 which discloses a bag with two open ends.

Typically, when performing tissue removal using endoscopic or laparoscopic techniques, it is necessary to have three separate devices inserted into the patient; the camera, a grasping/cutting device and a tissue retrieval bag. This means that at least three incisions need to be made in the patient, or an enlarged incision. Multiple incisions and/or enlarged incisions are not desirable for a patient.

Accordingly, it is desirable to provide a new and improved endoscopic/laparoscopic device.

SUMMARY OF THE INVENTION

Aspects of the present invention are set out in the attached claims.

According to an aspect of the present invention, there is provided a surgical device comprising an elongate shaft which extends from a proximal end region to a distal end region thereof, the shaft defining a retrieval lumen for receiving a tissue retrieval device therein, the retrieval lumen extending from the proximal end region to the distal end region of the elongate shaft, and having an open end at the distal end region of the elongate shaft; a tissue retrieval device which extends along the retrieval lumen, and which comprises a tissue retrieval bag having an end opening, and a manipulation device connected with the tissue retrieval bag and operable to move the tissue retrieval bag between a stowed configuration and a deployed configuration, the tissue retrieval bag being at least partially located within the retrieval lumen of the elongate shaft in the stowed configuration, and being external to the retrieval lumen in the deployed configuration, wherein the manipulation device comprises a connector component which slidably engages with and within a distal end portion of the retrieval lumen, the connector component defining an actuator channel therethrough from a proximal face to a distal face thereof, an actuation cord which extends through retrieval lumen, through the actuation channel of the connector component, and around the end opening of the retrieval bag; and an actuation grip located at the proximal end region of the elongate shaft and operable to actuate the actuation cord from a stowed position in which the retrieval bag is at least partially stowed in the retrieval lumen of the elongate shaft, and a deployed position in which the retrieval bag extends outside of the retrieval lumen of the elongate shaft.

In one example, the connector component defines a suction channel therethrough for the passage of fluid into the retrieval lumen.

In one example, the retrieval lumen defines a longitudinal axis, and comprises a proximal portion which extends from the proximal end region of the elongate shaft along the longitudinal axis, and a distal portion which extends from the distal end region of the elongate shaft along the longitudinal axis, wherein the proximal portion and the distal portion are contiguous, and wherein the proximal portion has a first dimension in a direction substantially perpendicular to the longitudinal axis of the third lumen, and wherein the distal portion has a second dimension greater than the first dimension in a direction substantially perpendicular to the longitudinal axis of the third lumen; and wherein the connector component has connector body which defines an outer surface complementary to the distal portion of the retrieval lumen.

In one example, the distal portion of the retrieval lumen is substantially oval or lozenge-shaped in longitudinal cross-section, and the connector body is substantially oval or lozenge-shaped in longitudinal cross-section.

One example further comprises a first lumen for receiving an elongate camera device therein, and a second lumen for receiving a tissue manipulation device therein, an elongate camera device which extends along the first lumen, and a tissue manipulation device which extends along the second lumen.

Such a surgical device is suitable for use in endoscopic surgical procedures, wherein the camera device is an endoscope, or is suitable for use in laparoscopic surgical procedures, wherein the camera device is a laparoscope.

Such a device is particularly suitable for use in bladder tumour removal.

Devices embodying the principles of the present invention may be provided for use in endoscopic or laparoscopic surgical procedures.

DETAILED DESCRIPTION OF THE PREFERRED EMBODIMENTS

Endoscopic or laparoscopic surgical techniques that are undertaken to remove tissue from a patient make use of a camera device, a tissue grasping/cutting device and a tissue removal device.

Figure 1:
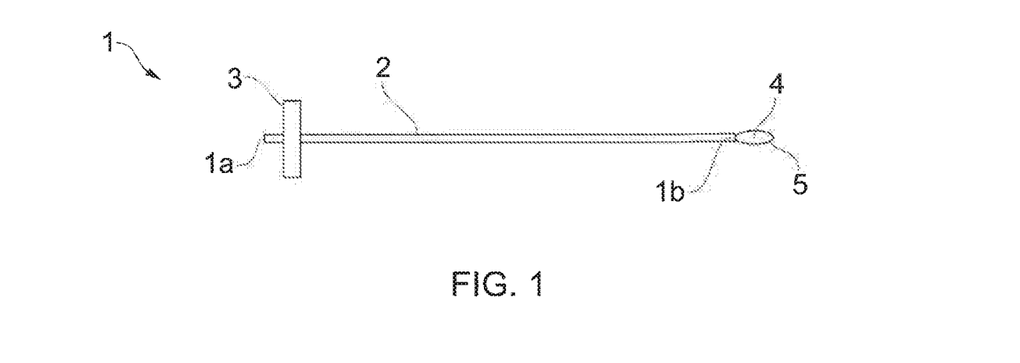
FIG. 1 is a schematic overview of a tissue retrieval device in a stowed configuration.

FIG. 1 is a schematic overview of a tissue retrieval device 1 in a stowed configuration. The device 1 comprises an elongate hollow shaft 2 which defines a lumen therealong. The lumen extends from a proximal end 1a of the device 1 to a distal end 1b of the device 1. The lumen has respective open ends at the proximal distal ends 1a and 1b of the device 1.

An actuation grip 3 (shown schematically for the sake of clarity) is located at the proximal end 1a of the device 1. A tissue retrieval bag 4 is in a stowed position substantially completely within the lumen of the hollow shaft 2 in the stowed configuration shown in FIG. 1. An actuation cord 5 extends around the retrieval bag 4 (to be described in more detail below), and extends through the open end of the lumen, along the lumen to the actuation grip 3. The actuation grip 3 engages with the actuation cord 5. The actuation cord 5 may be any suitable flexible cord, for example may be provided by a wire of suitable stiffness.

The shaft 2, actuation grip 3 and actuation cord 5 can be referred to as a manipulating device for the retrieval bag 4. The actuation grip 3 is movable between a stowed position (as shown in FIG. 1) in which the retrieval bag 4 is substantially contained within the lumen, and a deployed position (as shown in, and to be described with reference to, FIG. 2) in which the retrieval bag 4 is external to the lumen.

Figure 2:
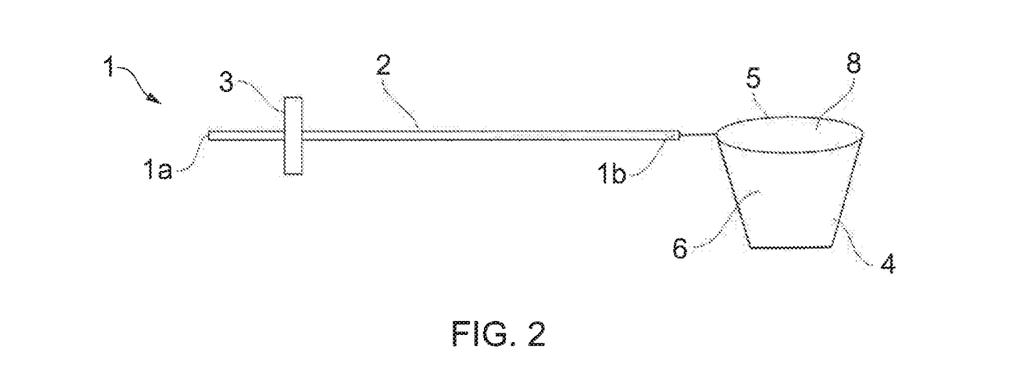
FIG. 2 is a schematic overview of a tissue retrieval device in a deployed configuration.

FIG. 2 illustrates the tissue retrieval device 1 of FIG. 1 in a deployed configuration. In this deployed configuration, the retrieval bag 4 is external to the lumen, having been moved from the stowed position by movement of the actuation cord 5 along the lumen such that the bag 4 is pushed out of the lumen. In the deployed configuration, the bag 4 expands to provide an inner volume 6. The inner volume 6 has an open aperture 8 through which tissue passes for retrieval. The actuation cord 5 serves to maintain the open aperture 8 in an open position.

Endoscopic and laparoscopic surgical techniques that make use of a camera and a tissue grasper/cutter require multiple incisions to be made in the patient. In accordance with the principles of embodiments of the present invention, a surgical device is provided that has an elongate shaft that is able to provide multiple lumens for the various devices required for a procedure. Such a combined device is particularly suited for use in bladder tumour removal procedures, and for retrieving a tissue sample without seeding of cells from that sample. This is particularly important when the sample is of a tumour.

Figure 3:
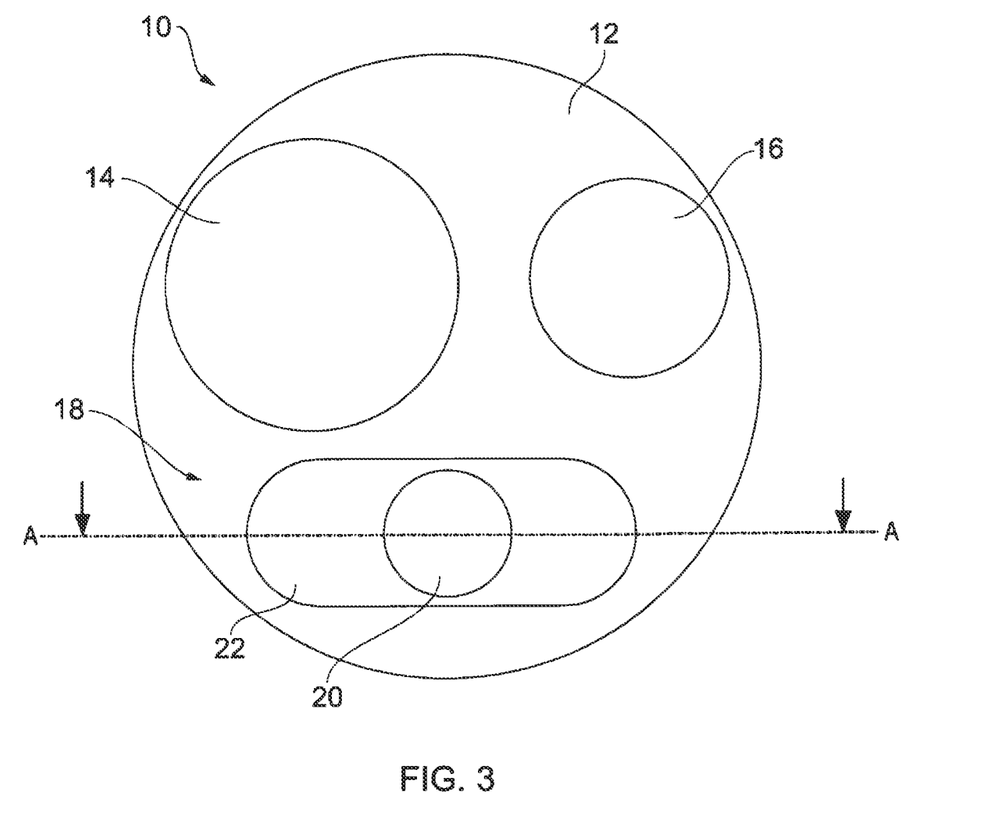
FIG. 3 is a schematic end view of a device shaft embodying one aspect of the present invention.

FIG. 3 is a schematic end view of an elongate shaft 12 for a surgical device 10 embodying an aspect of the present invention. The shaft 12 is extends from a proximal end region to a distal end region. FIG. 3 illustrates an end view of the distal end region. The shaft 12 defines a number of lumens that extend from the proximal end region to the distal end region. In the example shown in FIG. 3, three lumens are provided, each of which provides a location for a device, and each of which has an open end at the distal end region of the surgical device. The devices are not shown in FIG. 3 for the sake of clarity.

A first lumen 14 is of appropriate size for receiving an elongate camera device, such as an endoscope or a laparoscope. The camera device extends along and through the first lumen 14, so that images can be captured by the camera device from the distal end region of the shaft 12.

A second lumen 16 is of appropriate size for receiving a tissue manipulation device. The tissue manipulation device extends along the second lumen, and out of the distal end region thereof, in order that the surgeon using the device is able to grasp and manipulate tissue adjacent the distal end region of the surgical device. The camera device allows the surgeon to monitor the action of the manipulation device.

A third lumen 18 extends along the elongate shaft 12 for receiving a tissue retrieval device therein. The tissue removal device can be any appropriate device, for example a device as illustrated in FIGS. 1 and 2. The third lumen 18 comprises first and second portions 20 and 22. The first (proximal) portion 20 extends from the proximal end of the elongate shaft 12 towards the distal end, and the second (distal) portion 22 extends from the distal end of the first portion 20 to the distal end of the elongate shaft 12. The first and second portions 20 and 22 of the third lumen 18 are contiguous and form a continuous lumen from the proximal end region to the distal end of the elongate shaft 12. The second portion 22 provides an open distal end of the third lumen 18 at the distal end of the elongate shaft 12.

Figure 4:
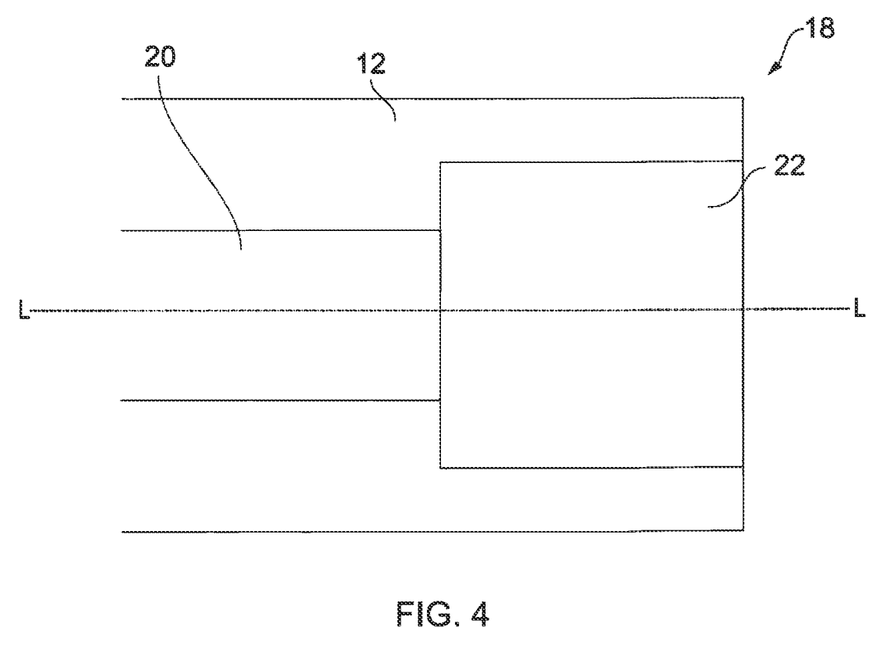
FIG. 4 is a schematic partial cross-sectional view of the device shaft of FIG. 3.
Figure 5:
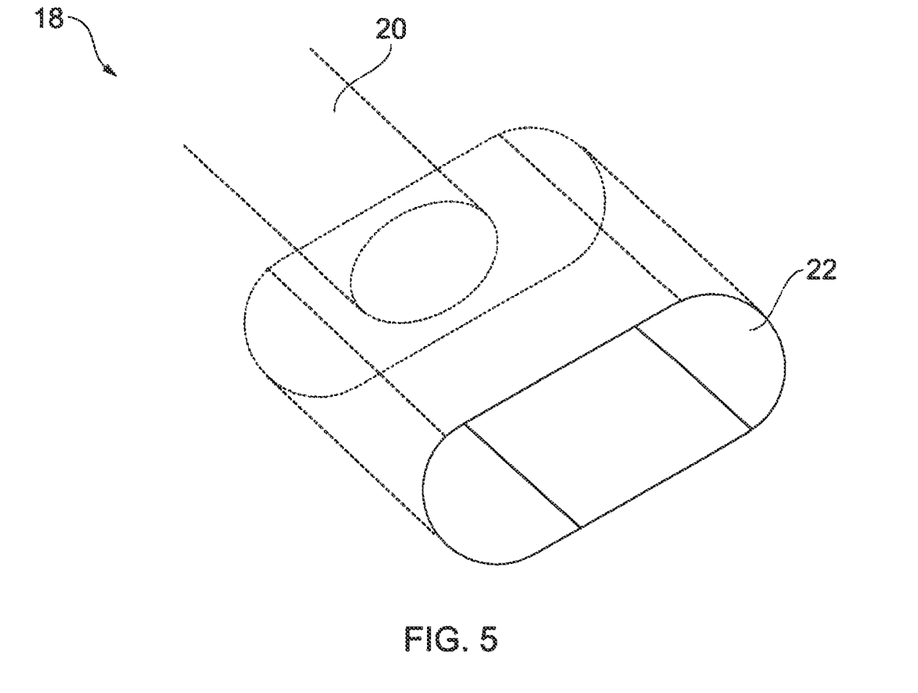
FIG. 5 is a schematic partial view of part of the device shaft of FIGS. 3 and 4.

FIG. 4 illustrates a partial transverse cross-sectional view of the distal end region of the elongate shaft 12, taken along line A-A of FIG. 3, and FIG. 5 illustrates a perspective view of the distal end region of the third lumen 18. As illustrated in FIGS. 3 and 4, the first and second portions 20 and 22 have respective first and second dimensions in a direction substantially perpendicular to the longitudinal axis L-L of the third lumen 18. The second dimension (of the second portion 22) is greater than the first dimension (of the first portion 20). The second portion 22 has a greater longitudinal cross-sectional area than the first portion 20. In one example, the second portion 22 is oval or lozenge-shaped in longitudinal cross-section. In one example, the first portion 20 is circular in longitudinal cross-section As such, the second portion 22 provides a location in which the retrieval bag of the tissue retrieval device can be stowed. The retrieval bag is fully or partially stowed within the second portion 22 by moving the actuation cord of the retrieval device into the stowed position, thereby pulling the retrieval bag partially or fully into the second portion 22. The change in cross sectional area between the second and first portions 22 and 20 provides the third lumen 18 with an effective stopper for the retrieval bag, which prevents the bag being pulled by a required distance within the third lumen 18.

The third lumen 18 also provides a suction pathway for the efficient removal of fluids and/or other material through the elongate shaft 12.

Figure 6:
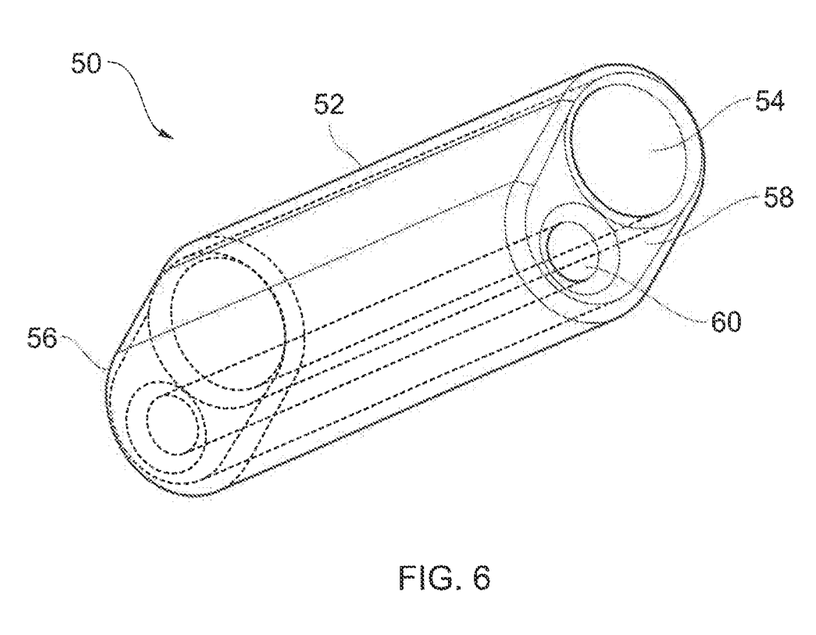
FIG. 6 is a schematic perspective view of a component embodying one aspect of the present invention for use with the device shaft of FIGS. 3 to 5.

FIG. 6 illustrates a connector component 50 embodying another aspect of the present invention, for use with the elongate shaft 12 of FIGS. 3 to 5. The connector component 50 has a connector body 52 has an outer shape which is complementary with the inner surface of the second portion 22 of the third lumen 18 of the elongate shaft 12. In the example shown in FIG. 6, the connector body 52 has an outer surface which may be described as lozenge-shaped or oval shaped. The connector body 52 is arranged to be engaged with the inner surface of the second portion 22 of the third lumen 18, so as to substantially seal that second portion 22.

The connector body 52 defines an actuator channel 54 therethrough. The actuator channel 54 extends from a proximal face 56 to a distal face 58 of the connector body 52, and provides respective open ends at those faces. The actuator channel 54 is arranged for the passage of the actuation cord of the tissue retrieval device therethrough. As mentioned, the actuation cord may be of any appropriate configuration, and may be provided by a multi-strand cable.

The cooperating shapes of the connector body 52 and the second portion 22 of the third lumen 18 enables the orientation of the tissue retrieval bag, relative to the first and second lumens 14 and 16, to be fixed. Such fixed orientation enables the tissue manipulation device to be inserted efficiently into the tissue retrieval bag.

The connector body 52 also defines a suction channel 60 therethrough. The suction channel 60 extends from the proximal face 56 to the distal face 58 of the connector body 52, and provides respective open ends at those faces. The suction channel 60 is arranged to hold a suction tube therein, so that the suction tube is held in an appropriate position relative to the retrieval bag. The suction tube is arranged to transfer fluids into the first portion 20 of the third lumen 18. The close fitting of the connector body 52 with the second portion 22 of the third lumen 18 effectively seals the second portion, which reduces, or eliminates leakage of fluid retrieved during use. In use, the proximal face 56 of the connector body 52 is spaced apart from the distal end of the first portion 20 of the third lumen 18, in order to provide a suction path for retrieved fluids.

When the tissue retrieval bag is moved into the stowed position, the connector body 52 is pulled at least partially into the second portion 22 of the third lumen 18, such that the proximal face 56 of the connector body 52 is engaged with the proximal face of the second portion 22 of the third lumen 18. When a connector component 50 is used, the tissue retrieval bag may be completely contained, or may be only partially contained, within the second portion 22 of the third lumen 18. Similarly, the suction tube may extend out of the suction channel 60 in both the deployed and stowed positions.

Figure 7:
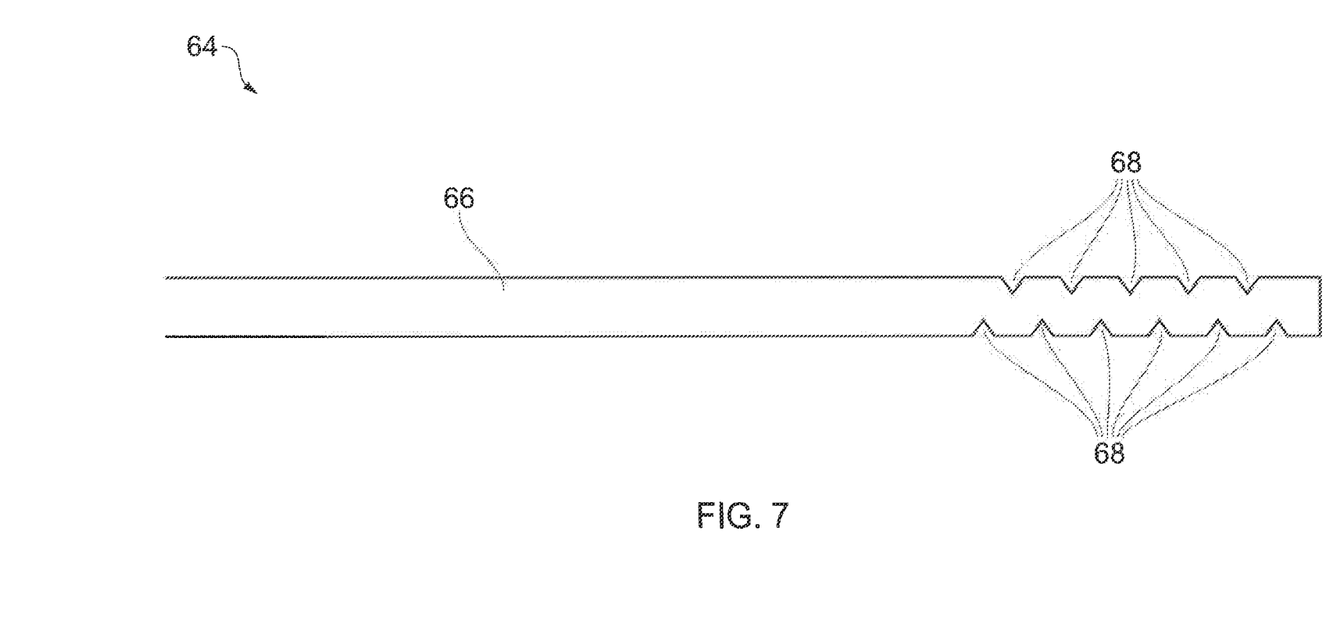
FIG. 7 is a schematic side view of a suction tube for use with the component of FIG. 6.

FIG. 7 illustrates schematically a side view of a suction tube 64 suitable for use with the connector component of FIG. 6. The suction tube comprises an elongate body 66, which defines a longitudinal passageway along its length. A plurality of apertures 68 are defined at a distal end portion of the body 66 to allow the transfer of fluids into the passageway, for transport along the passageway and out of a proximal end aperture of the tube 64. The body 66 is adapted for insertion into the suction channel 60 of the connector component 50 of FIG. 6.

The invention claimed is:

1. A surgical device comprising:
   an elongate shaft (i) which extends from a proximal end to a distal end and (ii) defining a retrieval lumen, the retrieval lumen (i) extending from the proximal end to the distal end of the elongate shaft and (ii) having an open end at the distal end of the elongate shaft; and
   a tissue retrieval device which (i) is received in the retrieval lumen, (ii) extends along the retrieval lumen, and (iii) comprises a tissue retrieval bag having an end opening and a manipulation device connected with the tissue retrieval bag and operable to move the tissue retrieval bag between a stowed configuration and a deployed configuration, the tissue retrieval bag being at least partially located within the retrieval lumen of the elongate shaft in the stowed configuration and being external to the retrieval lumen in the deployed configuration, wherein the manipulation device comprises:
   a connector component (i) which slidably engages a distal end of the retrieval lumen and (ii) defining (a) an actuator channel therethrough from a proximal face to a distal face thereof and (b) a suction channel therethrough for the passage of fluid into the retrieval lumen;
   an actuation cord which extends through the retrieval lumen, through the actuator channel of the connector component, and around the end opening of the retrieval bag; and
   an actuation grip located at the proximal end of the elongate shaft and operable to actuate the actuation cord from a stowed position in which the retrieval bag is at least partially stowed in the retrieval lumen of the elongate shaft and a deployed position in which the retrieval bag extends outside of the retrieval lumen of the elongate shaft.

2. A surgical device as claimed in claim 1, further comprising a first lumen for receiving an elongate camera device therein, and a second lumen for receiving a tissue manipulation device therein, an elongate camera device which extends along the first lumen, and a tissue manipulation device which extends along the second lumen.

3. A surgical device as claimed in claim 2, for use in endoscopic surgical procedures, wherein the camera device is an endoscope.

4. A surgical device as claimed in claim 2, for use in laparoscopic surgical procedures, wherein the camera device is a laparoscope.

5. A surgical device as claimed in claim 1, for use in bladder tumour removal.

6. A surgical device comprising:
   an elongate shaft (i) which extends from a proximal end to a distal end and (ii) defining a retrieval lumen, the retrieval lumen (i) extending from the proximal end to the distal end of the elongate shaft and (ii) having an open end at the distal end of the elongate shaft; and
   a tissue retrieval device which (i) is received in the retrieval lumen, (ii) extends along the retrieval lumen, and (iii) comprises a tissue retrieval bag having an end opening and a manipulation device connected with the tissue retrieval bag and operable to move the tissue retrieval bag between a stowed configuration and a deployed configuration, the tissue retrieval bag being at least partially located within the retrieval lumen of the elongate shaft in the stowed configuration and being external to the retrieval lumen in the deployed configuration, wherein:
   the manipulation device comprises:
   a connector component (i) which slidably engages a distal end of the retrieval lumen and (ii) defining an actuator channel therethrough from a proximal face to a distal face thereof;
   an actuation cord which extends through the retrieval lumen, through the actuator channel of the connector component, and around the end opening of the retrieval bag; and
   an actuation grip located at the proximal end of the elongate shaft and operable to actuate the actuation cord from a stowed position in which the retrieval bag is at least partially stowed in the retrieval lumen of the elongate shaft and a deployed position in which the retrieval bag extends outside of the retrieval lumen of the elongate shaft;

the retrieval lumen has a longitudinal axis and comprises a proximal portion which extends from the proximal end of the elongate shaft along the longitudinal axis and a distal portion which extends from the distal end of the elongate shaft along the longitudinal axis;

the proximal portion and the distal portion are contiguous;

the proximal portion has a first dimension in a direction substantially perpendicular to the longitudinal axis of the retrieval lumen;

the distal portion has a second dimension greater than the first dimension in the direction substantially perpendicular to the longitudinal axis of the retrieval lumen; and the connector component has connector body which defines an outer surface complementary to the distal portion of the retrieval lumen.

7. A surgical device as claimed in claim 6, wherein the proximal portion of the retrieval lumen is substantially circular in a longitudinal cross-section.

8. A surgical device as claimed in claim 6, wherein the distal portion of the retrieval lumen is substantially oval or lozenge-shaped in longitudinal cross-section, and the connector body is substantially oval or lozenge-shaped in longitudinal cross-section.

* * * * *